US006552026B2

(12) United States Patent
Pees et al.

(10) Patent No.: US 6,552,026 B2
(45) Date of Patent: Apr. 22, 2003

(54) 6-PHENYL-PYRAZOLOPYRIMIDINES

(75) Inventors: Klaus Jüergen Pees, Mainz (DE); Jordi Tormo i Blasco, Limbergerhof (DE); Hubert Sauter, Mannheim (DE); Oliver Cullman, Heppenheim (DE); Markus Gewehr, Kastellaun (DE); Wassilios Grammenos, Ludwigshafen (DE); Bernd Müller, Frankenthal (DE); Thomas Grote, Wachenheim (DE); Andreas Gypser, Mannheim (DE); Joachim Rheinheimer, Ludwigshafen (DE); Peter Schäfer, Ottersheim (DE); Frank Schieweck, Hessheim (DE); Eberhard Ammermann, Heppenheim (DE); Siegried Strathmann, Limburgerhof (DE); Gisela Lorenz, Hambach (DE); Rheinhard Stierl, Mutterstadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/735,033

(22) Filed: Dec. 12, 2000

(65) Prior Publication Data

US 2002/0049318 A1 Apr. 25, 2002

Related U.S. Application Data

(63) Continuation-in-part of application No. 09/566,340, filed on May 8, 2000, now abandoned.

(60) Provisional application No. 60/138,988, filed on Jun. 14, 1999.

(51) Int. Cl.$^7$ ..................... C07D 487/04; A61K 31/519

(52) U.S. Cl. ........................................ 514/258; 544/281

(58) Field of Search ........................... 514/258; 544/281

(56) References Cited

U.S. PATENT DOCUMENTS

| | | | | |
|---|---|---|---|---|
| 4,567,263 | A | 1/1986 | Eicken et al. | 544/263 |
| 5,817,663 | A | 10/1998 | Pees et al. | 544/263 |
| 5,902,773 | A | 5/1999 | Benoit et al. | 504/240 |
| 5,994,360 | A | 11/1999 | Pfrengle | 514/258 |
| 6,277,857 | B1 | 8/2001 | Pfrengle et al. | 514/258 |

FOREIGN PATENT DOCUMENTS

| | | |
|---|---|---|
| FR | 2765875 | 1/1999 |
| FR | 2784380 | 4/2000 |
| WO | 96/35690 | 11/1996 |

*Primary Examiner*—John M. Ford
(74) *Attorney, Agent, or Firm*—Keil & Weinkauf

(57) ABSTRACT

6-Phenyl-Pyrazolopyrimidines of formula I

I

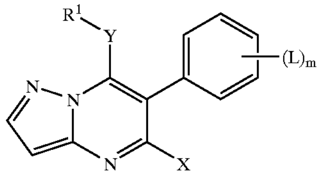

wherein $R^1$ is alkyl, alkenyl, alkynyl, alkadienyl or haloalkyl, cycloalkyl, bicycloalkyl, phenyl, naphthyl, or 5- or 6-membered heterocyclyl, containing one to four nitrogen atoms or one to three nitrogen atoms and one sulfur or oxygen atom, or 5- or 6-membered heteroaryl, containing one to four nitrogen atoms or one to three nitrogen atoms and one sulfur or oxygen atom, where these radicals may be unsubstituted or substituted as defined in the specification, Y is oxygen, sulfur, $NR^2$ or a single bond; wherein $R^2$is defined in the specification; and $R^1$ and $R^2$ together with the interjacent nitrogen atom may represent a 5- or 6-membered heterocyclic ring, containing one to four nitrogen atoms or one to three nitrogen atoms and one sulfur or oxygen atom, which may be substituted by one or more $R^c$ radicals;

m is 0 or an integer from 1 to 4;

L each independently is halogen, nitro, alkyl, alkoxy, and

X is halogen;

processes and intermediates for preparing these compounds, compositions comprising them and their use for controlling phytopathogenic fungi are described.

9 Claims, No Drawings

6-PHENYL-PYRAZOLOPYRIMIDINES

CROSS-REFERENCE TO RELATED APPLICATIONS

This is a continuation in part of application Ser. No. 09/566,340, filed on May 8, 2000, (now abandoned), which claims the benefit under 35 U.S.C. §119(e) of application Ser. No. 60/138,988, filed on Jun. 14, 1999, the entire disclosure of which is hereby incorporated by reference.

The present Invention relates to pyrazolopyrimidines of formula I

I

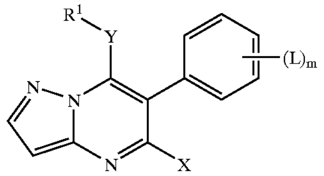

in which $R^1$ is $C_1$–$C_{10}$-alkyl, $C_2$–$C_{10}$-alkenyl, $C_2$–$C_{10}$-alkynyl, $C_2$–$C_{10}$-alkadienyl, or $C_1$–$C_{10}$-haloalkyl, where these radicals may be unsubstituted or partially or fully halogenated or may carry one to three groups $R^a$, $R^a$ is halogen, cyano, nitro, hydroxyl, $C_1$–$C_6$-alkyl, $C_1$–$C_6$-haloalkyl, $C_1$–$C_6$-alkylcarbonyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_2$–$C_6$-alkenyl, $C_2$–$C_6$-alkenyloxy, $C_3$–$C_6$-alkynyloxy and $C_1$–$C_4$-alkylenedioxy, which may be halogenated;

$C_3$–$C_8$-cycloalkyl, $C_5$–$C_{10}$-bicycloalkyl, phenyl, naphthyl, or 5- or 6-membered heterocyclyl, containing one to four nitrogen atoms or one to three nitrogen atoms and one sulfur or oxygen atom, or 5- or 6-membered heteroaryl, containing one to four nitrogen atoms or one to three nitrogen atoms and one sulfur or oxygen atom, where the cyclic systems may be partially or fully halogenated or may carry one to three groups $R^b$:

$R^b$ is halogen, cyano, nitro, hydroxyl, mercapto, amino, carboxyl, aminocarbonyl, aminothiocarbonyl, alkyl, haloalkyl, alkenyl, alkenyloxy, alkynyloxy, alkoxy, haloalkoxy, alkylthio, alkylamino, dialkylamino, formyl, alkylcarbonyl, alkylsulfonyl, alkylsulfoxyl, alkoxycarbonyl, alkylcarbonyloxy, alkylaminocarbonyl, dialkylaminocarbonyl, alkylaminothiocarbonyl, dialkylaminothiocarbonyl, where the alkyl groups in these radicals contain 1 to 6 carbon atoms and the abovementioned alkenyl or alkynyl groups in these radicals contain 2 to 8 carbon atoms;

Y is oxygen, sulfur, $NR^2$ or a single bond; wherein $R^2$ represents a hydrogen atom or $C_1$–$C_{10}$-alkyl, $C_2$–$C_{10}$-alkenyl, $C_2$–$C_{10}$-alkynyl, $C_2$–$C_{10}$-alkadienyl, $C_1$–$C_{10}$-haloalkyl, $C_3$–$C_8$-cycloalkyl, $C_5$–$C_{10}$-bicycloalkyl, phenyl, naphthyl, or 5- or 6-membered heterocyclyl, containing one to four nitrogen atoms or one to three nitrogen atoms and one sulfur or oxygen atom, or 5- or 6-membered heteroaryl, containing one to four nitrogen atoms or one to three nitrogen atoms and one sulfur or oxygen atom, where $R^2$ may be substituted by one or more $R^a$, or $R^1$ and $R^2$ together with the interjacent nitrogen atom represent a 5- or 6-membered heterocyclic ring, containing one to four nitrogen atoms or one to three nitrogen atoms and one sulfur or oxygen atom, which may be substituted by one or more $R^c$ radicals;

m is 0 or an integer from 1 to 4;

L each independently is halogen, nitro, $C_1$–$C_{10}$-alkyl, $C_1$–$C_{10}$-alkoxy, and X is halogen.

Moreover, the invention relates to processes for preparing these compounds, to compositions comprising them and to their use for controlling phytopathogenic fungi.

U.S. Pat. No. 4,567,263 discloses pyrazolopyrimidines which are substituted in the 7-Position by an unsubstituted amino group. These compounds are said to be active against various phytopathogenic fungi.

International Patent Application WO-A 96/35690 embraces pyrazolo-pyrimidines, to which a substituted phenyl is attached in the 2-position by a phenyl optionally via a linking group.

U.S. Pat. No. 5,817,663 discloses pyrazolopyrimidines, which are substituted by a pentafluorophenyl group in the 6-Position.

However, none of these documents discloses specifically 5-halopyrazolopyrimidines which are substituted in the 6-Position by a phenyl group having up to 4 substituents.

It is an object of the present invention to provide compounds having improved fungicidal activity.

We have found that this object is achieved by the compounds defined at the outset. Furthermore, we have found processes for their preparation, compositions comprising them and methods for controlling phytopathogenic fungi using the compounds I.

The present Invention further provides a process for the preparation of compounds of formula I as defined above which comprises treating a compound of formula IV

IV

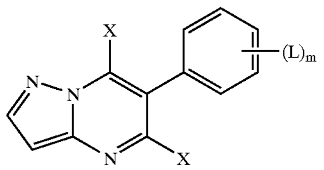

in which L, m and X are as defined in formula I; with an alcohol, amine or thiol of formula V $$R^1—Y—M \qquad V$$

in which $R^1$ and Y are as defined in formula I, and M represents a hydrogen atom or a free or complexed metal atom, to produce compounds of formula I.

For the preparation of the compounds wherein Y represents O, S or $NR^2$, M is preferably a hydrogen atom or a alkali metal.

For the preparation of the compounds wherein Y represents a single bond, M represents a free or complexed metal atom, such as for example Li, Mg or Zn in the presence of a transition metal, in particular Cu.

Compounds of formula IV are novel and can be prepared by reacting 5-amino-pyrazole with 2-phenyl-substituted malonic acid ester of formula II,

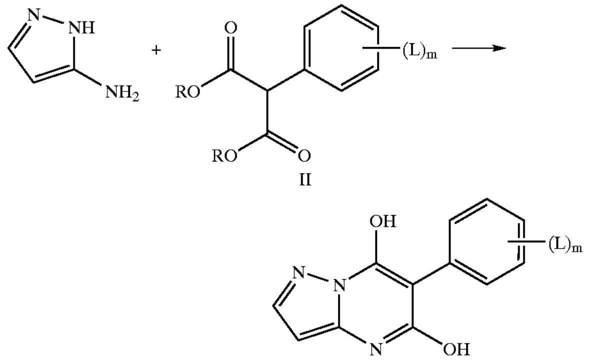

II

III wherein L and m are as defined for formula I, R represents alkyl, preferably $C_1$–$C_6$-alkyl, in particular methyl or ethyl, under alkaline conditions, preferably using high boiling tertiary amines as for example tri-n-butylamine as disclosed for example by EP-A 770 615.

The resulting 5,7-dihydroxy-6-phenyl-pyrazolopyrimidine of formula III

III

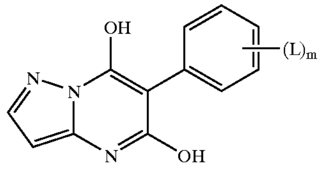

wherein L and m are as defined for formula I, is subsequently treated with a halogenating agent, preferably with a brominating or chlorinating agent, such as phosphorus oxybromide or phosphorus oxychloride, neat or in the presence of a solvent to give IV.

If phosphorus oxybromide or phosphorus oxychloride is used for the halogenation of III the presence of a mineralic acid, such as polyphosphoric acid, and pyridinium salts, preferably pyridinium halides, such as pyridinium bromide or chloride, is preferred.

The reaction is suitably carried out at a temperature in the range from 0° C. to 150° C., the preferred reaction temperature being from 80° C. to 125° C. as disclosed for example by EP-A 770 615.

The compounds of formula II are preferably prepared by reaction of the corresponding substituted bromobenzenes with sodium dialkylmalonates in the presence of a copper(I) salt, [e.g. Chemistry Letters, pp. 367–370, 1981].

Compounds of formula IVA are particularly preferred.

IVA

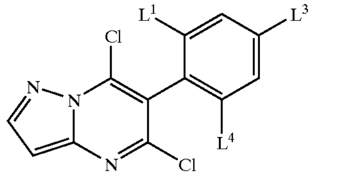

Accordingly, the Invention relates to the novel intermediates of formula IV, in particular 5,7-dichloro-6-(2,4,6-trifluorophenyl)pyrazolo[1,5-α]pyrimidine and 5,7-dichloro-6-(2-chloro-6-fluorophenyl)pyrazolo[1,5-α]pyrimidine, and to the corresponding 5,7-dihydroxy-6-phenyl-pyrazolo[1,5-α]pyrimidines of formula III.

The reaction between the 5,7-dihalogen-6-phenyl-pyrazolopyrimidines of formula IV and the compound of formula V, wherein Y is 0, S or $NR^2$, is preferably carried out in the presence of an inert solvent.

Suitable solvents include ethers, such as dioxane, diethyl ether and, especially, tetrahydrofuran, halogenated hydrocarbons such as dichloromethane and aromatic hydrocarbons, for example toluene.

The reaction is suitably carried out at a temperature in the range from 0° C. to 70° C., the preferred reaction temperature being from 10° C. to 35° C.

It is also preferred that the reaction is carried out in the presence of a base. Suitable bases include tertiary amines, such as triethylamine, and inorganic bases, such as potassium carbonate or sodium carbonate. Alternatively, an excess of the compound of formula V may serve as a base.

The reaction between the 5,7-dihalogen-6-phenyl-pyrazolopyrimidines of formula IV and the compound of formula V, wherein Y represents a single bond, is conveniently carried out in the presence of a solvent.

Suitable solvents include ethers, such as dioxane, diethyl ether and, especially, tetrahydrofuran, hydrocarbons such as hexane, cyclohexane or mineral oil, and aromatic hydrocarbons, for example toluene, or mixtures of these solvents.

The reaction is suitably carried out at a temperature in the range from −100° C. to +100° C., the preferred reaction temperature being from −80° C. to +40° C.

It is also preferred that the reaction is carried out in the presence of copper ions, preferably equimolar amounts of copper(I) halides, in particular copper(I) iodide.

Furthermore the compounds of formula I, wherein Y represents a single bond may be prepared by reacting the corresponding alkyl 2-aryl-3-alkyl-3-oxopropionates of formula VI

VI

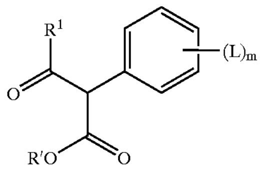

in which $R^1$, L and m have the meaning given and R' represents an optionally substituted alkyl group, preferably $C_1$–$C_4$-alkyl, with 5-amino-pyrazole.

The reaction mixtures are worked up in a customary manner, for example by mixing with water, phase separation and, if required, chromatographic purification of the crude products. Some of the intermediates and end products are obtained in the form of colorless or slightly brownish, viscous oils, which are purified or freed from volatile components under reduced pressure and at moderately elevated temperatures. If the intermediates and end products are obtained as solids, purification can also be carried out by recrystallization or digestion.

If individual compounds I are not obtainable by the routes described above, they can be prepared by derivatization of other compounds I.

However, if the synthesis yields isomer mixtures, a separation is generally not necessarily required since in some cases the individual isomers can be converted into one another during the preparation for use or upon use (for example under the action of light, acids or bases). Similar conversions may also occur after use, for example in the treatment of plants in the treated plant or in the harmful fungus or animal pest to be controlled.

In the symbol definitions given in the formulae above, collective terms were used which generally represent the following substituents:

halogen: fluorine, chlorine, bromine and iodine, especially bromine, chlorine or fluorine, in particular fluorine or chlorine;

$C_1$–$C_{10}$-alkyl and the alkyl moieties of alkoxy, alkadienyl, alkylthio, alkylamino or di-alkylamine: saturated, straight-chain or branched hydrocarbon radicals having 1 to 10, preferably 1 to 6 carbon atoms, especially 1 to 4 carbon atoms, specifically methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-di-methylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

$C_1$–$C_4$-alkylene: methylene, ethylene, n-propylene or n-butylene;

$C_1$–$C_{10}$-haloalkyl and the haloalkyl moieties of $C_1$–$C_{10}$-haloalkoxy: straight-chain or branched alkyl groups having 1 to 10, preferably 1 to 4 carbon atoms (as mentioned above), where the hydrogen atoms in these groups may be partially or fully replaced by halogen atoms as mentioned above, for example $C_1$–$C_2$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

$C_2$–$C_{10}$-alkenyl: unsaturated, straight-chain or branched hydrocarbon radicals having 2 to 10, preferably 2 to 6 carbon atoms and a double bond in any position, for example ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl and 2-methyl-2-propenyl;

$C_2$–$C_{10}$-alkynyl: straight-chain or branched hydrocarbon radicals having 2 to 10, preferably 1 to 4 carbon atoms and a triple bond in any position, for example ethynyl, 1-propynyl, 2-propynyl, 1-butynyl, 2-butynyl, 3-butynyl and 1-methyl-2-propynyl;

Cycloalkyl: monocyclic, saturated hydrocarbon groups with 3 to 6, 8, 10 or 12 carbon atoms, preferably $C_3$–$C_8$-cycloalkyl, specifically cyclopropyl, cyclobutyl, cyclopentyl, cyclohexyl, cycloheptyl and cyclooctyl.

Bicycloalkyl, as used herein with respect to a radical or moiety refers to a bicycloalkyl group having 5 to 10 carbon atoms, preferably 6 to 9 carbon atoms, in particular bicycloheptyl.

Aryl: a mono- to tricyclic aromatic ring system containing 6 to 14 carbon ring members, for example phenyl, naphthyl and anthracenyl;

5- or 6-membered heteroaryl, containing one to four nitrogen atoms or one to three nitrogen atoms and one sulfur or oxygen atom:

5-membered heteroaryl groups which, in addition to carbon atoms, may contain one to four nitrogen atoms or one to three nitrogen atoms and one sulfur or oxygen atom as ring members, for example 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl;

6-membered heteroaryl groups which, in addition to carbon atoms, may contain one to three or one to four nitrogen atoms as ring members, for example 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl.

5- or 6-membered heterocyclyl, containing one to four nitrogen atoms or one to three nitrogen atoms and one sulfur or oxygen atom: 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydro-triazin-2-yl and 1,2,4-hexahydrotriazin-3-yl;

Optionally by $R^a$ or $R^b$ substituted moieties may be unsubstituted or have from one up to the maximal possible number of substituents. Typically, 0 to 2 substituents are present.

Preferred meanings for $R^a$ and $R^b$ radicals are: halogen, nitro, cyano, hydroxy, $C_1$–$C_6$-alkyl, $C_3$–$C_6$-cycloalkyl, $C_3$–$C_6$-cycloalkenyl, $C_1$–$C_6$ haloalkyl, $C_3$–$C_6$-halocycloalkyl, $C_1$–$C_6$-alkoxy, $C_1$–$C_6$ haloalkoxy, tri-$C_1$–$C_4$-alkylsilyl, phenyl, halo- or dihalo-phenyl or pyridyl.

The Invention especially relates to compounds of the formula I in which any alkyl or haloalkyl part of the groups $R^1$ or $R^2$, which may be straight chained or branched, contains up to 10 carbon atoms, preferably 1 to 9 carbon atoms, more preferably 2 to 6 carbon atoms, any alkenyl or alkynyl part of the substituents $R^1$ or $R^2$ contains up to 10 carbon atoms, preferably 2 to 9 carbon atoms, more preferably 3 to 6 carbon atoms, any cycloalkyl part of the substituents $R^1$ or $R^2$ contains from 3 to 10 carbon atoms, preferably from 3 to 8 carbon atoms, more preferably from 3 to 6 carbon atoms, any bicycloalkyl part of the substituents $R^1$ or $R^2$ contains from 5 to 9 carbon atoms, preferably from 7 to 9 carbon atoms and any aryl part of the substituent $R^1$ or $R^2$ contains 6, 10 or 14 carbon atoms, preferably 6 or 10 carbon atoms. Any alkyl, alkenyl or alkynyl group may be linear or branched.

The Invention especially relates to compounds of the formula I in which $R^1$ represents a straight-chained or branched $C_1$–$C_{10}$ alkyl,in particular a branched $C_3$–$C_{10}$-alkyl group, a $C_3$–$C_8$-cycloalkyl, a $C_5$–$C_9$-bicycloalkyl, a $C_3$–$C_8$-cycloalkyl-$C_1$–$C_6$-alkyl, $C_1$–$C_{10}$-alkoxy-$C_1$–$C_6$-alkyl, a $C_1$–$C_{10}$-haloalkyl or a phenyl group being optionally substiuted by one to three halogen atoms or $C_1$–$C_{10}$-alkyl or $C_1$–$C_{10}$-alkoxy groups.

The particularly preferred embodiments of the intermediates with respect to the variables correspond to those of the radicals X, Y, $R^1$, $R^2$, L and m of formula I.

A preferred alkyl moiety in formula I is ethyl or especially methyl.

A preferred haloalkyl moiety in formula I is 2,2,2-trifluoroethyl or 1,1,1-trifluoroprop-2-yl.

A preferred alkenyl moiety in formula I is allyl or especially 2-methylallyl.

Preferred heterocyclyl moieties in formula I are pyrrolodinyl, pyrazolidinyl, piperidinyl, piperazinyl or morpholin-4-yl.

Preferred heteroaryl moieties in formula I are: pyridyl, pyrimidyl, pyrazolyl or thienyl.

Cyclic groups in formula I are preferably optionally substituted by one or more halogen atoms, nitro, cyano, $C_1$–$C_6$-alkyl, or $C_1$–$C_6$-alkoxy.

Compounds of formula I are preferred wherein X denotes a fluorine, chlorine or bromine atom, in particular a chlorine atom.

Particular preference is given to compounds of formula I wherein Y represents $NR^2$ or a single bond, in particular $NR^2$.

Moreover, particular preference is given to compounds of formula I in which $R^2$ is hydrogen.

Besides, particular preference is given to compounds of the formula I in which Y denotes $NR^2$ and $R^2$ is hydrogen, $C_1$–$C_{10}$-alkyl or $C_1$–$C_{10}$-haloalkyl, in particular hydrogen.

If $R^1$ denotes $C_1$–$C_{10}$-haloalkyl, preferably a polyfluorinated alkyl group, in particular a 2,2,2-trifluoroethyl, a 2-(1,1,1-trifluoropropyl) or a 2-(1,1,1-trifluorobutyl) group, $R^2$ preferably is hydrogen.

If $R^1$ denotes an optionally substituted $C_3$–$C_8$-cycloalkyl group, preferably a cyclopentyl or cyclohexyl group, $R^2$ preferably is hydrogen or $C_1$–$C_6$-alkyl.

Particular preference is also given to compounds of the formula I in which X is $NR^2$ and $R^1$ and $R^2$ together with the interjacent nirogen atom form an optionally substituted heterocyclic ring, preferably an optionally substituted $C_3$–$C_7$-heterocyclic ring, in particular a pyrolidine, piperidine, tetra hydropyridine, in paricular 1,2,3,6-tetrahydropyridine or azepane ring which is optionally substituted by one or more $C_1$–$C_6$-alkyl, $C_1$–$C_6$-haloalkyl or $C_1$–$C_6$-alkoxy groups, preferably by one $C_1$–$C_6$-alkyl group.

L preferably is halogen or $C_1$–$C_6$-alkoxy. A preferred embodiment are compounds of formula I in which

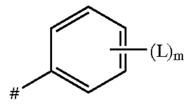

represents

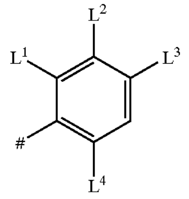

wherein # denotes the link to the pyrazolopyrimidine moiety, $L^1$ through $L^4$ each independently represent hydrogen, especially fluorine, chlorine, methyl or methoxy, in particular wherein $L^1$ is fluoro, $L^2$ is hydrogen or fluoro, $L^3$ is hydrogen or fluoro or methoxy and $L^4$ denotes hydrogen, fluoro chloro or methyl.

Moreover, particular preference is given to compounds of the formula I in which m is 2 or 3. Most preferred $L^4$ is not hydrogen.

Furthermore, particular preference is given to compounds of formula IA in which the variables have the meaninng as defined in formula I.

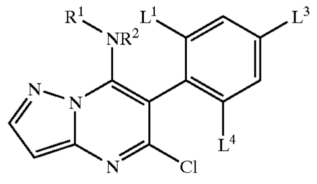

IA

Preference is given to compounds of formula IA in which $L^1$ denotes halogen and $L^3$ and $L^4$ each independently represent hydrogen, halogen or $C_1$–$C_4$-alkoxy.

Included in the scope of the present Invention are (R) and (S) isomers of compounds of general formula I having a chiral center and the racemates thereof, and salts, N-Oxides and acid addition compounds.

Particularly preference is given to compounds of formula IA wherein $R^2$ is hydrogen, $L^1$ and $L^4$ independently represent fluorine or chlorine atoms, and $L^3$ denotes hydrogen, fluorine, chlorine or methoxy.

Likewise, preference is given for the following compounds of formula I:

[5-chloro-6-(2,4,6-trifluoro-phenyl)-pyrazolo[1,5-α]pyrimidin-7-yl]-(2,2,2-trifluoro-ethyl)-amine,

[5-chloro-6-(2,4,6-trifluorophenyl)-pyrazolo[1,5-α]pyrimidin-7-yl]-cyclopentyl-amine,

[5-chloro-6-(2,4,6-trifluoro-phenyl)-pyrazolo[1,5-α]pyrimidin-7-yl]-(1,1,1-trifluoro-prop-2-yl)-amine,

[5-chloro-6-(2,4,6-trifluoro-phenyl)-pyrazolo[1,5-α]pyrimidin-7-yl]-diethyl-amine,

[5-chloro-6-(2,4,6-trifluoro-phenyl)-pyrazolo[1,5-α]pyrimidin-7-yl]-isopropyl-amine,
sec-butyl-[5-chloro-6-(2,4,6-trifluorophenyl)-pyrazolo[1,5-α]pyrimidin-7-yl]-amine,
bicyclo[2.2.1]hept-2-yl-[5-chloro-6-(2,4,6-trifluoro-phenyl)-pyrazolo[1,5-α]pyrimidin-7-yl]-amine,
[5-chloro-6-(2-chloro-6-fluoro-phenyl)-pyrazolo[1,5-α]pyrimidin-7-yl]cyclopentyl-amine,
[5-chloro-6-(2-chloro-6-fluoro-phenyl)-pyrazolo[1,5-α]pyrimidin-7-yl]-(2,2,2-trifluoro-ethyl)-amine,
[5-chloro-6-(2-chloro-6-fluoro-phenyl)-pyrazolo[1,5-α]pyrimidin-7-yl]-(1,1,1-trifluoro-prop-2-yl)-amine,
[5-chloro-6-(2-chloro-6-fluoro-phenyl)pyrazolo[1,5-α]pyrimidin-7-yl]-diethyl-amine,
[5-chloro-6-(2-chloro-6-fluoro-phenyl)-pyrazolo[1,5-α]pyrimidin-7-yl]-isopropyl-amine,
sec-butyl-[5-chloro-6-(2-chloro-6-fluoro-phenyl)-pyrazolo[1,5-α]pyrimidin-7-yl]amine,
bicyclo[2.2.1]hept-2-yl-(5-chloro-6-(2-chloro-6-fluoro-phenyl)pyrazolo[1,5-α]pyrimidin-7-yl]-amine,
[5-chloro-6-(2,6-difluoro-4-methoxyphenyl)-pyrazolo[1,5-α]pyrimidin-7-yl]-(2,2,2-trifluoro-ethyl)-amine,
[5-chloro-6-(2,4,6-trifluoro-phenyl)-pyrazolo[1,5-α]pyrimidin-7-yl]-4-methyl-cyclohexane,
[5-chloro-6-(2-chloro-6-fluoro-phenyl)-pyrazolo[1,5-α]pyrimidin-7-yl]-4-methyl-cyclohexane, and
[5-chloro-6-(2,4,6-trifluoro-phenyl)-pyrazolo[1,5-α]pyrimidin-7-yl]-4-fluoro-cyclohexane.

Moreover, particular preference is given to following compounds:
[5-chloro-6-(2,4,6-trifluoro-phenyl)-7-(4-methyl-piperidin-1-yl)-1,2,4]triazolo[1,5-α]pyrimidine;
[5-chloro-6-(2,4,6-trifluoro-phenyl)-pyrazolo[1,5-α]pyrimidin-7-yl]-(2,2,2-trifluoro-ethyl)amine;
[5-chloro-6-(2,4,6-trifluoro-phenyl)-pyrazolo[1,5-α]pyrimidin-7-yl]cyclopentyl-amine;
[5-chloro-6-(2,4,6-trifluoro-phenyl)-pyrazolo[1,5-α]pyrimidin-7-yi]-(1,1,1-trifluoro-prop-2yl)-amine;
[5-chloro-6-(2,4,6-trifluoro-phenyl)-pyrazolo[1,5-α]pyrimidin-7-yl]-diethylamine;
[5-chloro-6-(2,4,6-trifluoro-phenyl)-pyrazolo[1,5-α]pyrimidin-7-yl]isopropyl-amine;
sec-butyl-[5-chloro-6-(2,4,6-trifluoro-phenyl)-pyrazolo[1,5-α]pyrimidin-7-yl]-amine;
bicyclo[2.2.1]hept-2-yl-[5-chloro-6-(2,4,6-trifluoro-phenyl)-pyrazolo[1,5-α]pyrimidin-7-yl]amine;
[5-chloro-6-(2-chloro-6-fluoro-phenyl)-pyrazolo[1,5-α]pyrimidin-7-yl]cyclopentyl-amine;
[5-chloro-6-(2-chloro-6-fluoro-phenyl)-pyrazolo[1,5-α]pyrimidin-7-yl](2,2,2-trifluoroethyl)-amine;
[5-chloro-6-(2-chloro-6-fluoro-phenyl)-pyrazolo[1,5-α]pyrimidin-7-yl](1,1,1-trifluoroprop-2-yl)-amine;
[5-chloro-6-(2-chloro-6-fluoro-phenyl)-pyrazolo[1,5-α]pyrimidin-7-yl]diethyl-amine;
[5-chloro-6-(2-chloro-6-fluoro-phenyl)-pyrazolo[1,5-α]pyrimidin-7-yl]isopropyl-amine;
sec-butyl-[5-chloro-6-(2-chloro-6-fluoro-phenyl)-pyrazolo[1,5-α]pyrimidin-7-yl]-amine;
[5-chloro-6-(2,6-difluoro-4-methoxyphenyl)-pyrazolo[1,5-α]pyrimidin-7-yl](1,1,1-trifluoroprop-2-yl)-amine;
bicyclo[2.2.1]hept-2-yl-[5-chloro-6-(2-chloro-6-fluoro-phenyl)-pyrazolo[1,5-α]pyrimidin-7-yl]-amine.

With respect to their use, particular preference is given to the compounds I compiled in the tables below. The groups mentioned in the table for a substituent are furthermore for their part, independently of the combination in which they are mentioned, a particularly preferred embodiment of the respective substituents.

Table 1

Compounds of the formula IA, in which $L^1$ is fluoro, $L^3$ is hydrogen, $L^4$ is chloro and $R^1$ and $R^2$ correspond to one row in Table A Table 2

Compounds of the formula IA, in which $L^1$ and $L^4$ each are fluoro, $L^3$ is hydrogen and $R^1$ and $R^2$ correspond to one row in Table A Table 3

Compounds of the formula IA, in which $L^1$ and $L^4$ each are chloro, $L^3$ is hydrogen and $R^1$ and $R^2$ correspond to one row in Table A Table 4

Compounds of the formula IA, in which $L^1$ is methyl, $L^3$ is hydrogen, $L^4$ is fluoro and $R^1$ and $R^2$ correspond to one row in Table A Table 5

Compounds of the formula IA, in which $L^1$, $L^3$ and $L^4$ each are fluoro and $R^1$ and $R^2$ correspond to one row in Table A Table 6

Compounds of the formula IA, in which $L^1$ and $L^4$ each are fluoro, $L^3$ is methoxy and $R^1$ and $R^2$ correspond to one row in Table A

TABLE A

IA

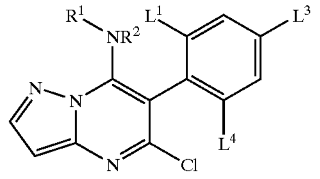

| No. | $R^1$ | $R^2$ |
|---|---|---|
| A-1 | $CH_2CH_3$ | H |
| A-2 | $CH_2CH_3$ | $CH_3$ |
| A-3 | $CH_2CH_3$ | $CH_2CH_3$ |
| A-4 | $CH_2CH_2CH_3$ | H |
| A-5 | $CH_2CH_2CH_3$ | $CH_3$ |
| A-6 | $CH_2CH_2CH_3$ | $CH_2CH_3$ |
| A-7 | $CH_2CH_2CH_3$ | $CH_2CH_2CH_3$ |
| A-8 | $CH_2CF_3$ | H |
| A-9 | $CH_2CF_3$ | $CH_3$ |
| A-10 | $CH_2CF_3$ | $CH_2CH_3$ |
| A-11 | $CH_2CF_3$ | $CH_2CH_2CH_3$ |
| A-12 | $CH_2CCl_3$ | H |
| A-13 | $CH_2CCl_3$ | $CH_3$ |
| A-14 | $CH_2CCl_3$ | $CH_2CH_3$ |
| A-15 | $CH_2CCl_3$ | $CH_2CH_2CH_3$ |
| A-16 | $CH(CH_3)_2$ | H |
| A-17 | $CH(CH_3)_2$ | $CH_3$ |
| A-18 | $CH(CH_3)_2$ | $CH_2CH_3$ |
| A-19 | $CH(CH_3)_2$ | $CH_2CH_2CH_3$ |
| A-20 | (±) $CH(CH_2CH_3)CH_3$ | H |
| A-21 | (±) $CH(CH_2CH_3)CH_3$ | $CH_3$ |
| A-22 | (±) $CH(CH_2CH_3)CH_3$ | $CH_2CH_3$ |
| A-23 | (R) $CH(CH_2CH_3)CH_3$ | H |
| A-24 | (R) $CH(CH_2CH_3)CH_3$ | $CH_3$ |
| A-25 | (R) $CH(CH_2CH_3)CH_3$ | $CH_2CH_3$ |
| A-26 | (S) $CH(CH_2CH_3)CH_3$ | H |
| A-27 | (S) $CH(CH_2CH_3)CH_3$ | $CH_3$ |
| A-28 | (S) $CH(CH_2CH_3)CH_3$ | $CH_2CH_3$ |
| A-29 | (±) $CH(CH_3)—CH(CH_3)_2$ | H |
| A-30 | (±) $CH(CH_3)—CH(CH_3)_2$ | $CH_3$ |
| A-31 | (±) $CH(CH_3)—CH(CH_3)_2$ | $CH_2CH_3$ |
| A-32 | (R) $CH(CH_3)—CH(CH_3)_2$ | H |

TABLE A-continued

IA

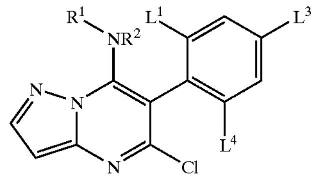

| No. | $R^1$ | $R^2$ |
| --- | --- | --- |
| A-33 | (R) $CH(CH_3)$—$CH(CH_3)_2$ | $CH_3$ |
| A-34 | (R) $CH(CH_3)$—$CH(CH_3)_2$ | $CH_2CH_3$ |
| A-35 | (S) $CH(CH_3)$—$CH(CH_3)_2$ | H |
| A-36 | (S) $CH(CH_3)$—$CH(CH_3)_2$ | $CH_3$ |
| A-37 | (S) $CH(CH_3)$—$CH(CH_3)_2$ | $CH_2CH_3$ |
| A-38 | (±) $CH(CH_3)$—$C(CH_3)_3$ | H |
| A-39 | (±) $CH(CH_3)$—$C(CH_3)_3$ | $CH_3$ |
| A-40 | (±) $CH(CH_3)$—$C(CH_3)_3$ | $CH_2CH_3$ |
| A-41 | (R) $CH(CH_3)$—$C(CH_3)_3$ | H |
| A-42 | (R) $CH(CH_3)$—$C(CH_3)_3$ | $CH_3$ |
| A-43 | (R) $CH(CH_3)$—$C(CH_3)_3$ | $CH_2CH_3$ |
| A-44 | (S) $CH(CH_3)$—$C(CH_3)_3$ | H |
| A-45 | (S) $CH(CH_3)$—$C(CH_3)_3$ | $CH_3$ |
| A-46 | (S) $CH(CH_3)$—$C(CH_3)_3$ | $CH_2CH_3$ |
| A-47 | (±) $CH(CH_3)$—$CF_3$ | H |
| A-48 | (±) $CH(CH_3)$—$CF_3$ | $CH_3$ |
| A-49 | (±) $CH(CH_3)$—$CF_3$ | $CH_2CH_3$ |
| A-50 | (R) $CH(CH_3)$—$CF_3$ | H |
| A-51 | (R) $CH(CH_3)$—$CF_3$ | $CH_3$ |
| A-52 | (R) $CH(CH_3)$—$CF_3$ | $CH_2CH_3$ |
| A-53 | (S) $CH(CH_3)$—$CF_3$ | H |
| A-54 | (S) $CH(CH_3)$—$CF_3$ | $CH_3$ |
| A-55 | (S) $CH(CH_3)$—$CF_3$ | $CH_2CH_3$ |
| A-56 | (±) $CH(CH_3)$—$CCl_3$ | H |
| A-57 | (±) $CH(CH_3)$—$CCl_3$ | $CH_3$ |
| A-58 | (±) $CH(CH_3)$—$CCl_3$ | $CH_2CH_3$ |
| A-59 | (R) $CH(CH_3)$—$CCl_3$ | H |
| A-60 | (R) $CH(CH_3)$—$CCl_3$ | $CH_3$ |
| A-61 | (R) $CH(CH_3)$—$CCl_3$ | $CH_2CH_3$ |
| A-62 | (S) $CH(CH_3)$—$CCl_3$ | H |
| A-63 | (S) $CH(CH_3)$—$CCl_3$ | $CH_3$ |
| A-64 | (S) $CH(CH_3)$—$CCl_3$ | $CH_2CH_3$ |
| A-65 | $CH_2C(CH_3){=}CH_2$ | H |
| A-66 | $CH_2C(CH_3){=}CH_2$ | $CH_3$ |
| A-67 | $CH_2C(CH_3){=}CH_2$ | $CH_2CH_3$ |
| A-68 | cyclopentyl | H |
| A-69 | cyclopentyl | $CH_3$ |
| A-70 | cyclopentyl | $CH_2CH_3$ |
| A-71 | —$(CH_2)_2CH(CH_3)(CH_2)_2$— | |

Due to excellent activity, the compounds of formula I may be used in cultivation of all plants where infection by phytopathogenic fungi is not desired, e.g. cereals, solanaceous crops, vegetables, legumes, apples, vine.

The compounds according to formula I are superior through their valuable fungicidal properties, in particular their enhanced systemicity and enhanced fungicitoxity.

Moreover, the compounds I are suitable for controlling harmful fungi such as Paecilomyces variotii in the protection of materials (e.g. wood, paper, paint dispersions, fibers and tissues) and in the protection of stored products.

The compounds I are applied by treating the fungi, or the plants, seeds, materials or the soil to be protected against fungal infection, with a fungicidally active amount of the active ingredients. Application can be effected both before and after infection of the materials, plants or seeds by the fungi.

In general, the fungicidal compositions comprise from 0.1 to 95, preferably 0.5 to 90, % by weight of active ingredient.

When used in crop protection, the rates of application are from 0.01 to 2.0 kg of active ingredient per ha, depending on the nature of the effect desired.

In the treatment of seed, amounts of active ingredient of from 0.001 to 0.1 g, preferably 0.01 to 0.05 g, are generally required per kilogram of seed.

When used in the protection of materials or stored products, the rate of application of active ingredient depends on the nature of the field of application and on the effect desired. Rates of application conventionally used in the protection of materials are, for example, from 0.001 g to 2 kg, preferably 0.005 g to 1 kg, of active ingredient per cubic meter of material treated.

For example, they can be used in agriculture or related fields for the control of phytopathogenic fungi such as *Alternaria solani, Botrytis cinerea, Cercospora arachidicola, Cercospora beticola, Cladosporium herbarum, Cochliobolus miyabeanus, Corticium rolfsii, Erysiphe graminis, Erysiphe cichoracearum und Sphaerotheca fuliginea, Fusarium-species, Erysiphe cichoracearum, Helminthosporium tritici repentis, Leptosphaeria nodorum, Micronectriella nivalis, Monilinia fructigena, Mycosphaerella ligulicola, Mycosphaerella pinodes, Phytophthora infestans, Plasmopara viticola, Pseudocercosporella herpotrichoides,* Puccinia-species, *Pyricularia oryzae, Rhizoctonia solani, Sclerotinia sclerotiorum, Sphaerotheca fuliginea, Uncinula necator* and *Venturia inequalis.* The compounds of formula I according to the Invention possess a high fungicidal activity within a wide concentration range.

The Invention further provides a fungicidal composition which comprises an active ingredient, which is at least one compound of formula I as defined above, and one or more carriers. A method of making such a composition is also provided which comprises bringing a compound of formula I as defined above into association with the carrier(s). Such a composition may contain a single active ingredient or a mixture of several active ingredients of the present Invention. It is also envisaged that different isomers or mixtures of isomers may have different levels or spectra of activity and thus compositions may comprise individual isomers or mixtures of isomers.

A composition according to the Invention preferably contains from 0.5% to 95% by weight (w/w) of active ingredient.

A carrier in a composition according to the Invention is any material with which the active ingredient is formulated to facilitate application to the locus to be treated, which may for example be a plant, seed, soil, or water in which a plant grows, or to facilitate storage, transport or handling. A carrier may be a solid or a liquid, including material which is normally a gas but which has been compressed to form a liquid.

The compositions may be manufactured into e.g. emulsion concentrates, solutions, oil in water emulsions, wettable powders, soluble powders, suspension concentrates, dusts, granules, water dispersible granules, micro-capsules, gels, tablets and other formulation types by well-established procedures. These procedures include intensive mixing and/or milling of the active ingredients with other substances, such as fillers, solvents, solid carriers, surface active compounds (surfactants), and optionally solid and/or liquid auxiliaries and/or adjuvants. The form of application such as spraying, atomizing, dispersing or pouring may be chosen like the compositions according to the desired objectives and the given circumstances.

Solvents may be aromatic hydrocarbons, e.g. Solvesso® 200, substituted naphthalenes, phthalic acid esters, such as dibutyl or dioctyl phthalate, aliphatic hydrocarbons, e.g. cyclohexane or paraffins, alcohols and glycols as well as their ethers and esters, e.g. ethanol, ethyleneglycol monoand dimethyl ether, ketones such as cyclohexanone, strongly polar solvents such as N-methyl-2-pyrrolidone, or γ-butyrolactone, higher alkyl pyrrolidones, e.g. noctylpyrrolidone or cyclohexylpyrrolidone, epoxidized plant oil esters, e.g. methylated coconut or soybean oil ester and water. Mixtures of different liquids are often suitable.

Solid carriers, which may be used for dusts, wettable powders, water dispersible granules, or granules, may be mineral fillers, such as calcite, talc, kaolin, montmorillonite or attapulgite. The physical properties may be improved by addition of highly dispersed silica gel or polymers. Carriers for granules may be porous material, e.g. pumice, kaolin, sepiolite, bentonite; non-sorptive carriers may be calcite or sand. Additionally, a multitude of pre-granulated inorganic or organic materials may be used, such as dolomite or crushed plant residues.

Pesticidal compositions are often formulated and transported in a concentrated form which is subsequently diluted by the user before application. The presence of small amounts of a carrier which is a surfactant facilitates this process of dilution. Thus, preferably at least one carrier in a composition according to the invention is a surfactant. For example, the composition may contain at two or more carriers, at least one of which is a surfactant.

Surfactants may be nonionic, anionic, cationic or zwitterionic substances with good dispersing, emulsifying and wetting properties depending an the nature of the compound according to general formula I to be formulated. Surfactants may also mean mixtures of individual surfactants.

The compositions of the Invention may for example be formulated as wettable powders, water dispersible granules, dusts, granules, tablets, solutions, emulsifiable concentrates, emulsions, suspension concentrates and aerosols.

Wettable powders usually contain 5 to 90% w/w of active ingredient and usually contain in addition to solid inert carrier, 3 to 10% w/w of dispersing and wetting agents and, where necessary, 0 to 10% w/w of stabilizer(s) and/or other additives such as penetrants or stickers. Dusts are usually formulated as a dust concentrate having a similar composition to that of a wettable powder but without a dispersant, and may be diluted in the field with further solid carrier to give a composition usually containing 0.5 to 10% w/w of active ingredient.

Water dispersible granules and granules are usually prepared to have a size between 0.15 mm and 2.0 mm and may be manufactured by a variety of techniques. Generally, these types of granules will contain 0.5 to 90% w/w active ingredient and 0 to 20% w/w of additives such as stabilizer, surfactants, slow release modifiers and binding agents. The so-called "dry flowables" consist of relatively small granules having a relatively high concentration of active ingredient.

Emulsifiable concentrates usually contain, in addition to a solvent or a mixture of solvents, 1 to 80% w/v active ingredient, 2 to 20% w/v emulsifiers and 0 to 20% w/v of other additives such as stabilizers, penetrants and corrosion inhibitors. Suspension concentrates are usually milled so as to obtain a stable, nonsedimenting flowable product and usually contain 5 to 75% w/v active ingredient, 0.5 to 15% w/v of dispersing agents, 0.1 to 10% w/v of suspending agents such as protective colloids and thixotropic agents, 0 to 10% w/v of other additives such as defoamers, corrosion inhibitors, stabilizers, penetrants and stickers, and water or an organic liquid in which the active ingredient is substantially insoluble; certain organic solids or inorganic salts may be present dissolved in the formulation to assist in preventing sedimentation and crystalization or as antifreeze agents for water.

Aqueous dispersions and emulsions, for example compositions obtained by diluting the formulated product according to the Invention with water, also lie within the scope of the Invention.

Of particular interest in enhancinig the duration of the protective activity of the compounds of this invention is the use of a carrier which will provide slow release of the pesticidal compounds into the environment of a plant which is to be protected.

The biological activity of the active ingredient can also be increased by including an adjuvant in the spray dilution. An adjuvant is defined here as a substance which can increase the biological activity of an active ingredient but is not itself significantly biologically active. The adjuvant can either be included in the formulation as a coformulant or carrier, or can be added to the spray tank together with the formulation containing the active ingredient.

As a commodity the compositions may preferably be in a concentrated form whereas the end user generally employs diluted compositions. The compositions may be diluted to a concentration down to 0.001% of active ingredient. The doses usually are in the range from 0.01 to 10 kg a.i./ha.

Examples of formulations according to the Invention are:

| | | |
|---|---|---|
| Emulsion Concentrate (EC) | | |
| Active Ingredient | Compound of Example 5 | 30% (w/v) |
| Emulsifier(s) | Atlox ® 4856 / Atlox ® 4858 B[1)] (mixture containing calcium alkyl aryl sulfonate, fatty alcohol ethoxylates and light aromatics / mixture containing calcium alkyl aryl sulfonate, fatty alcohol ethoxylates and light aromatics) | 5% (w/v) |
| Solvent | Shellsol ® A[2)] (mixture of $C_9$–$C_{10}$ aromatic hydrocarbons) | to 1000 ml |
| Suspension Concentrate (SC) | | |
| Active Ingredient | Compound of Example 5 | 50% (w/v) |
| Dispersing agent | Soprophor ® FL[3)] (polyoxyethylene polyaryl phenyl ether phosphate amine salt) | 3% (w/v) |
| Antifoaming agent | Rhodorsil ® 422[3)] (nonionic aqueous emulsion of polydimethylsiloxanes) | 0.2% (w/v) |
| Structure agent | Kelzan ® S[4)] (Xanthan gum) | 0.2% (w/v) |
| Antifreezing agent | Propylene glycol | 5% (w/v) |
| Biocidal agent | Proxel ® [5)] (aqueous dipropylene glycol solution containing 20% 1,2-benisothiazolin-3-one) | 0.1% (w/v) |
| Water | | to 1000 ml |
| Wettable Powder (WP) | | |
| Active Ingredient | Compound of Example 7 | 60% (w/w) |
| Wetting agent | Atlox ® 4995[1)] (polyoxyethylene alkyl ether) | 2% (w/w) |
| Dispersing agent | Witcosperse ® D-60[6)] (mixture of sodium salts of condensed naphthalene sulfonic acid and alkylarylpolyoxy acetates | 3% (w/w) |
| Carrier / Filler | Kaolin | 35% (w/w) |
| Water Dispersible Granules (WG) | | |
| Active Ingredient | Compound of Example 7 | 50% (w/w) |
| Dispersing / Binding agent | Witcosperse ® D-450[6)] (mixture of sodium salts of condensed naphthalene sulfonic acid and alkyl sulfonates) | 8% (w/w) |

-continued

| | | |
|---|---|---|
| Wetting agent | Morwet ® EFW[6) (formaldehyde condensation product) | 2% (w/w) |
| Antifoaming agent | Rhodorsil ® EP 6703[3) (encapsulated silicone) | 1% (w/w) |
| Disintegrant | Agrimer ® ATF[7) (cross-linked homopolymer of N-vinyl-2-pyrrolidone) | 2% (w/w) |
| Carrier / Filler | Kaolin | 35% (w/w) |

[1)commercially available from ICI Surfactants
[2)commercially available from Deutsche Shell AG
[3)commercially available from Rhône-Poulenc
[4)commercially available from Kelco Co.
[5)commercially available from Zeneca
[6)commercially available from Witco
[7)commercially available from International Speciality Products The compositions of this Invention can be applied to the plants or their environment simultaneous with or in succession with other active substances. These other active substances can be either fertilisers, agents which donate trace elements or other preparations which influence plant growth. However, they can also be selective herbicides, insecticides, fungicides, bactericides, nematicides, algicides, molluscicides, rodenticides, virucides, compounds inducing resistance into plants, biological control agents such as viruses, bacteria, nematodes, fungi and other microorganisms, repellents of birds and animals, and plant growth regulators, or mixtures of several of these preparations, if appropriate together with other carrier substances conventionally used in the art of formulation, surfactants or other additives which promote application.

The other fungicidal compound can be, for example, one which is also capable of combating diseases of cereals (e.g. wheat) such as those caused by Erysiphe, Puccinia, Septoria, Gibberella and Helminthosporium spp., seed and soil Borne diseases and downy and powdery mildews on vines, early and late blight an solanaceous crops, and powdery mildew and scab an apples etc. These mixtures of fungicides can have a broader spectrum of activity than the compound of general formula I alone.

Examples of the other fungicidal compounds are anilazine, azoxystrobin, benalaxyl, benomyl, binapacryl, bitertanol, blasticidin S, Bordeaux mixture, bromuconazole, bupirimate, captafol, captan, carbendazim, carboxin, carpropamid, chlorbenzthiazon, chlorothalonil, chlozolinate, copper-containing compounds such as copper oxychloride, and copper sulfate, cycloheximide, cymoxanil, cypofuram, cyproconazole, cyprodinil, dichlofluanid, dichlone, dichloran, diclobutrazol, diclocymet, diclomezine, diethofencarb, difenoconazole, diflumetorim, dimethirimol, dimethomorph, diniconazole, dinocap, ditalimfos, dithianon, dodemorph, dodine, edifenphos, epoxiconazole, etaconazole, ethirimol, etridiazole, famoxadone, fenapanil, fenamidone, fenarimol, fenbuconazole, fenfuram, fenhexamid, fenoxanil, fenpiclonil, fenpropidin, fenpropimorph, fentin, fentin acetate, fentin hydroxide, ferimzone, fluazinam, fludioxonil, flumetover, fluquinconazole, flusilazole, flusulfamide, flutolanil, flutriafol, folpet, fosetyl-aluminium, fuberidazole, furalaxyl, furametpyr, guazatine, hexaconazole, IKF-916, imazalil, iminoctadine, ipconazole, iprodione, isoprothiolane, iprovalicarb, kasugamycin, KH-7281, kitazin P, kresoxim-methyl, mancozeb, maneb, mepanipyrim, mepronil, metalaxyl, metconazole, methfuroxam, MON 65500, myclobutanil, neoasozin, nicket dimethyldithiocarbamate, nitrothalisopropyl, nuarimol, ofurace, organo mercury compounds, oxadixyl, oxycarboxin, penconazole, pencycuron, phenazineoxide, phthalide, picoxystrobin, polyoxin D, polyram, probenazole, prochloraz, procymidione, propamocarb, propiconazole, propineb, pyraclostrobin, pyrazophos, pyrifenox, pyrimethanil, pyroquilon, pyroxyfur, quinomethionate, quinoxyfen, quintozene, spiroxamine, SSF-126, SSF-129, streptomycin, sulfur, tebuconazole, tecloftalame, tecnazene, tetraconazole, thiabendazole, thifluzamide, thiophanate-methyl, thiram, tolclofosmethyl, tolylfluanidt triadimefon, triadimenol, triazbutil, triazoxide, tricyclazole, tridemorph, trifloxystrobin, triflumizole, triforine, triticonazole, validamycin A, vinclozolin, XRD-563, zarilamid, zineb, ziram.

In addition, the co-formulations according to the Invention may contain at least one compound of formula I and any of the following classes of biological control agents such as viruses, bacteria, nematodes, fungi, and other microorganisms which are suitable to control insects, weeds or plant diseases or to induce host resistance in the plants. Examples of such biological control agents are: *Bacillus thuringiensis, Verticillium lecanü, Autographics californica NPV, Beauvaria bassiana, Ampelomyces quisqualis, Bacilis subtuis, Pseudomonas chlororaphis, Pseudomonas fluorescens, Steptomyces griseoviridis* and *Trichoderma harzianum.*

Moreover, the co-formulations according to the Invention may contain at least one compound of formula I and a chemical agent that induces the systemic acquired resistance in plants such as for example isonicotinic acid or derivatives thereof, 2,2-dichloro-3,3-dimethylcyclopropanecarboxylic acid or BION.

The compounds of general formula I can be mixed with soil, pest or other rooting media for the protection of the plants against seed-borne, soil-borne or foliar fungal diseases.

The Invention still further provides the use as a fungicide of a compound of formula I as defined above or a composition as defined above, and a method for combating fungus at a locus, which comprises treating the locus, which may be for example plants subject to or subjected to fungal attack, seeds of such plants or the medium in which such plants are growing or are to be grown, with such a compound or composition.

The present Invention is of wide applicability in the protection of crop and ornamental plants against fungal attack. Typical crops which may be protected include eines, grain crops such as wheat and barley, rice, sugar beet, top fruit, peanuts, potatoes, vegetables and tomatoes. The duration of the protection is normally dependent an the individual compound selected, and also a variety of external factors, such as climate, whose impact is normally mitigated by the use of a suitable formulation.

The following examples further illustrate the present Invention. It should be understood, however, that the Invention is not limited solely to the particular examples given below.

EXAMPLE 1

Preparation of diethyl (2,4,6-trifluoro-phenyl)-malonate

Diethyl malonate (0.49 mol) was added to a mixture of sodium hydride (0.51 mol) and 1,4-dioxane (140 ml) at 55 to 60° C. within 2 hours. A mixture of 1,4-dioxane (50 ml) and diethyl malonate (0.13 mol) was added. The mixture was stirred for 10 minutes at 55° C. and copper(I) bromide (0.05 mol) was added. After 15 min. a mixture of 2-bromo-1,3,5-trifluorobenzene (0.25 mol) and 1,4-dioxane (10 ml) was added. The reaction mixture was heated at 100° C. for 15 hours and cooled to 15° C. Hydrochloric acid (12N, 35 ml) was added slowly at 15 to 20° C. The precipitate was filtered off. The filtrate was extracted with diethylether. The organic Phase was separated, dried with anhydrous sodium sulphate and filtered. The filtrate was evaporated under reduced Pressure to yield the product.

Diethyl (2-chloro-6-fluoro-phenyl)-malonate was obtained analogously.

EXAMPLE 2

Preparation of 5,7-dihydroxy-6-(2,4,6-trifluoro-phenyl)-pyrazolo[1,5-α]pyrimidine A mixture of 3-amino-pyrazole (0.06 mol), diethyl (2,4,6-trifluorophenyl)-malonate (0.06 mol, obtained from Example 1) and tributylamine (30 ml) was heated with reflux at 175° C. for four hours. The reaction mixture was cooled to 100° C. Aqueous sodium hydroxide (10.3 g/120 ml $H_2O$) was added and the reaction mixture was stirred for 30 min. and cooled to ambient temperature. The organic Phase was separated off and the aqueous Phase was extracted with diethylether. The aqueous Phase was acidified with concentrated hydrochloric acid. The precipitate was collected by filtration and dried to yield 15.7 g (93 %) of the pale yellow product having a melting point of 280° C.

EXAMPLE 3 a

Preparation of 5,7-dichloro-6-(2,4,6-trifluoro-phenyl)-pyrazolo[1,5-α]pyrimidine A mixture of 5,7-dihydroxy-(2,4,6-trifluoro-phenyl)-pyrazolo [1,5-α]pyrimidine (0.053 mol, obtained from Example 2) and phosphorous oxychloride (50 ml) was heated with reflux for 16 hours and cooled to ambient temperature. The mixture was filtered and the excess of phosphorous oxychloride was distilled off. The residue was poured into a mixture of dichloromethane and water. The organic layer was separated, dried with sodium sulphate and filtered. The filtrate was concentrated in vacuo and then purified by flash chromatography (diethylether/petrol ether 1:2 v/v) to yield 2.4 g of the title compound as beige crystals having a melting point of 136–138° C.

EXAMPLE 3 b

Preparation of 5,7-dichloro-6-(2,4,6-trifluoro-phenyl)-pyrazolo[1,5-α]pyrimidine A mixture of 5,7-dihydroxy-(2,4,6-trifluoro-phenyl)-pyrazolo[1,5-α]pyrimidine (2 g, 7.1 mmol), pyridinium chloride (1.8 g, 15.5 mmol), polyphosphoric acid (0.6 g, 6.1 mmol) and phosphorous oxychloride (30 ml) was heated with reflux for 16 hours and cooled to ambient temperature. The mixture was filtered off and the excess of phosphorous oxychloride was distilled off. The residue was poured into a mixture of dichloromethane and water. The organic layer was separated, dried with sodium sulphate and filtered. The filtrate was concentrated in vacuo and the purified by flash chromatography (diethylether/petrol ether 1:2 v/v) to yield 1.8 g of white crystals having a melting point of 136–138° C.

EXAMPLE 4

Preparation of [5-chloro-6-(2,4,6-trifluoro-phenyl)-pyrazolo[1,5-α]pyrimidin-7-yl]-(2,2,2-trifluoroethyl)-amine [I-7]

A mixture of 2,2,2-trifluoroethylamine (10 ml) and 5,7-dichloro(2,4,6-trifluoro-phenyl)pyrazolo[1.5-α]pyrimidine (3.0 mmoles) was stirred for 3 days at ambient temperature. The reaction mixture was subsequently treated with a mixture of dichloromethane and aqueous hydrochloric acid (5%). The organic layer was separated, dried with anhydrous sodium sulphate and filtered. The filtrate was evaporated under reduced pressure to yield 0.2 g of the title compound as a yellowish powder having a melting point of 138° C.

EXAMPLES 5–12

The following examples (Table I; structure and melting point) are synthesized analogously to Example 4.

TABLE I

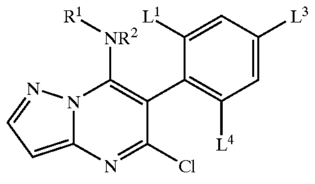

| No. | $R^1$ | $R^2$ | $L^1$ | $L^3$ | $L^4$ | Phys. Data (m.p. [° C.]) |
|---|---|---|---|---|---|---|
| I-5 | $-(CH_2)_2-CH(CH_3)-(CH_2)_2-$ | | F | F | F | 173 |
| I-6 | cyclopentyl | H | F | F | F | 128 |
| I-7 | 2,2,2-trifluoroethyl | H | F | F | F | 138 |
| I-8 | ethyl | ethyl | F | F | F | 90 |
| I-9 | $CH_2C(CH_3)=CH_2$ | ethyl | F | F | F | 89 |
| I-10 | n-propyl | n-propyl | F | F | F | oil |
| I-11 | iso-propyl | H | F | F | F | 143 |
| I-12 | iso-propyi | methyl | F | F | F | 109 |

EXAMPLE 13

Preparation of 5-chloro-7-n-hexyl-6-(2,4,6-trifluorophenyl)-pyrazolo[1,5-α]pyrimidine Copper iodide (5 mmol) was suspended in THF (25 ml) under an inert gas atmosphere. The suspension was cooled to −70° C. and n-hexyllithium (5 ml,2M in hexanes) was added by syringe. The mixture was stirred for 45 minutes and 5,7-dichloro-6-(2,4,6-trifluorophenyl)-pyrazolo[1,5-α] pyrimidine (5 mmol, obtained from Example 3) was added as a solution in THF (10 min). The reaction mixture was stirred for 15 minutes at −70° C. The reaction mixture was then quenched with a mixture of aqueous saturated ammonium chloride/concentrated ammonia (9:1). The two phase mixture was separated. An oil was isolated from the organic layer which was subjected to chromatographic purification which yields the product as a crystalline residue.

EXAMPLES 14–26

The following examples (Table II) are synthesized analogously to Example 13.

TABLE II

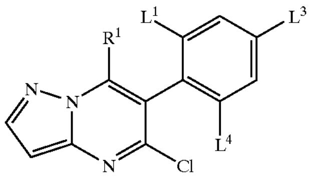

| No. | $R^1$ | $L^1$ | $L^3$ | $L^4$ | Phys. Data (m.p. [° C.]) |
|---|---|---|---|---|---|
| II-14 | n-heptyl | F | F | F | |
| II-15 | cyclopentyl | F | F | F | |
| II-16 | cyclohexyl | F | F | F | |
| II-17 | 4-methylcyclohexyl | F | F | F | |
| II-18 | 2-methylpropyl | F | F | F | |
| II-19 | n-heptyl | F | H | Cl | |
| II-20 | cyclopentyl | F | H | Cl | |
| II-21 | cyclohexyl | F | H | Cl | |
| II-22 | n-hexyl | F | H | Cl | |
| II-23 | 4-methylcyclohexyl | F | H | Cl | |
| II-24 | 2-methylpropyl | F | H | Cl | |
| II-25 | 4-fluorocyclohexyl | F | F | F | |
| II-26 | 4-fluorocyclohexyl | F | $OCH_3$ | F | |

Biological Investigations

Determination of Minimum Inhibitory Concentration by Test Compounds in the Serial Dilution Test with Pyricularia Orvzae The MIC (Minimum Inhibitory Concentration) value, which indicates the lowest concentration of the active ingredient in the growth medium which causes a total inhibition of myecelial growth, is determined by serial dilution tests using Microtiter plates with 24 or 48 wells per plate. The dilution of the test compounds in the nutrient solution and the distribution to the wells is carried out by a TECAN RSP 5000 Robotic Sample Processor. The following test compound concentrations are used: 0.05, 0.10, 0.20, 0.39, 0.78, 1.56, 3.13, 6.25, 12.50, 25.00, 50.00 and 100.00 μg/ml. For preparation of the nutrient solution, V8 vegetable juice (333 ml) is mixed with calcium carbonate (4.95 g), centrifuged, the supernatant (200 ml) diluted with water (800 ml) and autoclaved at 121° C. for 30 min.

The inocula of Pyricularia oryzae are added into the wells as spore suspensions (50 μl; $5\times10^5$/ml) or agar slices (6 mm) of an agar culture of the fungus.

After 6–12 days incubation at suitable temperatures (18–25° C.), the MIC values are determined by visual inspection of the plates (Table III).

TABLE III

| Example No. | MIC [μg/ml] |
|---|---|
| I-5 | 0.78 |
| I-7 | 0.78 |

What is claimed is:

1. A pyrazolopyrimidine compound of formula I

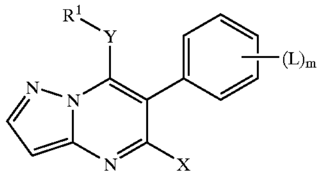

I in which $R^1$ is $C_1$–$C_{10}$-alkyl, $C_2$–$C_{10}$-alkenyl, $C_2$–$C_{10}$-alkynyl, or $C_1$–$C_{10}$-haloalkyl, where these radicals are unsubstituted or partially of fully halogenated or carry one to three groups $R^a$;

$C_3$–$C_8$-cycloalkyl, $C_5$–$C_{10}$-bicycloalkyl, phenyl or naphthyl, where the cyclic systems are unsubstituted or partially or fully halogenated or carry one to three groups $R^b$;

Y is $NR^2$ or a single bond;

$R^2$ represents a hydrogen atom or $C_1$–$C_{10}$-alkyl, $C_2$–$C_{10}$-alkenyl, $C_2$–$C_{10}$-alkynyl, $C_1$–$C_{10}$-haloalkyl, $C_3$–$C_8$-cycloalkyl, $C_5$–$C_{10}$-bicycloalkyl, phenyl or naphthyl, and $R^2$ is optionally substituted by one or more of $R^a$;

m is 0 or an integer from 1 to 4;

L each independently is halogen, nitro, $C_1$–$C_{10}$-alkyl, $C_1$–$C_{10}$-alkoxy;

X is halogen;

$R^a$ is halogen, cyano, nitro, hydroxyl, $C_1$–$C_6$-alkyl, $C_1$–$C_6$-haloalkyl, $C_1$–$C_6$-alkylcarbonyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_2$–$C_6$-alkenyl, $C_2$–$C_6$-alkenyloxy, $C_3$–$C_6$-alkynyloxy and $C_1$–$C_4$-alkylenedioxy, which may be halogenated; and $R^b$ is halogen, cyano, nitro, hydroxyl, mercapto, amino, carboxyl, aminocarbonyl, aminothiocarbonyl, alkyl, haloalkyl, alkenyl, alkenyloxy, alkynyloxy, alkoxy, haloalkoxy, alkylthio, alkylamino, dialkylamino, formyl, alkylcarbonyl, alkylsulfonyl, alkylsulfoxyl, alkoxycarbonyl, alkylcarbonyloxy, alkylaminocarbonyl, dialkylaminocarbonyl, alkylaminothiocarbonyl, dialkylaminothiocarbonyl, where the alkyl groups in these radicals contain 1 to 6 carbon atoms and the abovementioned alkenyl or alkynyl groups in these radicals contain 2 to 8 carbon atoms.

2. The compound defined in claim 1, in which Y represents $NR^2$.

3. The compound defined in claim 1, in which $R^1$ is $C_1$–$C_6$-alkyl, $C_1$–$C_6$-haloalkyl or $C_2$–$C_6$-alkenyl, and $R^2$ is hydrogen or $C_1$–$C_6$-alkyl.

4. The compound defined in claim 1, in which

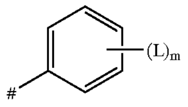

represents

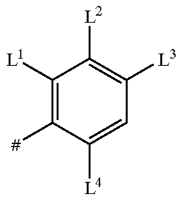

wherein $L^1$ is fluoro, $L^2$ is hydrogen or fluoro, $L^3$ is hydrogen, fluoro or methoxy and $L^4$ is hydrogen, fluoro, chloro or methyl, and # denotes the link to the pyrazolopyrimidyl moiety.

5. The compound defined in claim 4, in which m is 1, 2 or 3, and $L^4$ is fluoro, chloro or methyl.

6. A process for preparing the compound of formula I defined in claim 1, which comprises reacting 5-aminopyrazole

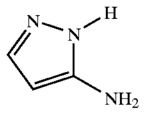

with a 2-phenyl malonic acid ester of formula II,

II

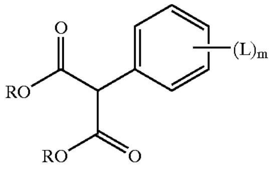

wherein R denotes $C_1$–$C_6$-alkyl, under alkaline conditions, to obtain a compound of formula III,

III

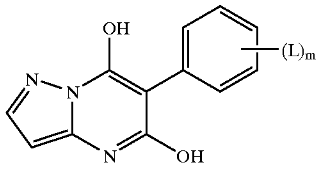

subsequently treating the compound of formula III with a halogenating agent to obtain a compound of formula IV

IV

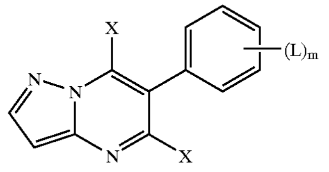

then treating the compound of formula IV with an amine of formula V $R^1$—Y—M V in which M represents a hydrogen atom or a free or complexed metal atom, to obtain the compound of formula I.

7. A compound of formula IV

IV

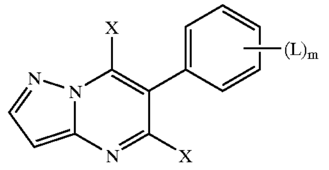

wherein m is 0 or an integer from 1 to 4;

L each independently is halogen, nitro, $C_1$–$C_{10}$-alkyl, $C_1$–$C_{10}$-alkoxy, and X is halogen.

8. A composition suitable for controlling phytopathogenic fungi, comprising a solid or liquid carrier and the compound of formula I defined in claim 1.

9. A method for controlling phytopathogenic fungi, which comprises treating the fungi or materials, plants, soil or seed to be protected against fungal attack with an effective amount of the compound of formula I defined in claim 1.

* * * * *

UNITED STATES PATENT AND TRADEMARK OFFICE

CERTIFICATE OF CORRECTION

PATENT NO. : 6,552,026 B2
DATED : April 22, 2003
INVENTOR(S) : Pees et al.

It is certified that error appears in the above-identified patent and that said Letters Patent is hereby corrected as shown below:

Title page,
Item [75], Inventors, the last inventor, "Rheinhard Stierl" should be
-- Reinhard Stierl --.

Item [57], ABSTRACT,
Line 10, after formula I, "Y is oxygen, sulfur" should start a new line;
Line 11, after formula I, "$R^2$is" should be -- $R^2$ is --.

Column 20,
Line 17, "or partially of" should be -- or partially or --.

Signed and Sealed this

Eighth Day of July, 2003

JAMES E. ROGAN
*Director of the United States Patent and Trademark Office*